United States Patent [19]

Kikuchi et al.

[11] Patent Number: 5,198,355
[45] Date of Patent: Mar. 30, 1993

[54] PURIFICATION OF GLYCOSAMINOGLYCAN DEGRADING ENZYMES WITH A SULFATED POLYSACCHARIDE

[75] Inventors: Hiroshi Kikuchi, Saitama; Ken-ichi Maeyama; Keiichi Yoshida, both of Tokyo, all of Japan

[73] Assignee: Seikagaku Kogyo Co., Ltd., Tokyo, Japan

[21] Appl. No.: 397,942

[22] Filed: Aug. 24, 1989

[30] Foreign Application Priority Data

Aug. 24, 1988 [JP] Japan ................... 63-208154

[51] Int. Cl.$^5$ .................. C12N 9/88; C12N 11/12; C12N 11/02
[52] U.S. Cl. .................... 435/232; 435/179; 435/177
[58] Field of Search ............ 435/232, 179, 177

[56] References Cited

U.S. PATENT DOCUMENTS

| | | | |
|---|---|---|---|
| 3,549,500 | 12/1970 | Suzuki ................... | 435/232 |
| 4,138,292 | 2/1979 | Chibata et al. ......... | 435/179 |
| 4,490,467 | 12/1984 | Jarman et al. .......... | 435/232 |
| 4,574,117 | 3/1986 | Vollmer et al. ......... | 435/232 |
| 4,609,625 | 9/1986 | Keyes et al. ........... | 435/177 |

FOREIGN PATENT DOCUMENTS 1060513 3/1989 United Kingdom .

OTHER PUBLICATIONS

Patel, *Purification of Ehzymes-Affinity Chromatography*, Biotechnology—applications and research, 1985.
Liau et al, *Heterogeneity of Rat Rib Chondroitin . . .* Biochimica et Biophysica Acta, 539, pp. 315–323, 1978.
Meyer et al, *Evidence for a Mechanical Coupling of . . .* Biochimica et Biophysica Acta, 755, pp. 376–387, 1983.
Wu et al, *Analysis of glycosaminoglycans in . . .* Biochimica et Biophysica Acta, 938, pp. 107–113, 1988.
Carbohydrate Research, 70, 295–306 (1979).
Carbohydrate Research, 88, 291–303 (1981).
Eur. J. Biochem., 145, 607–615 (1984).
Federation Proceedings, 36, 43 (1977).
J. Biol. Chem., 243, 1536 (1968).
Enzymology, 28, 902 (1972).
Enzymology, 28, 663 (1972).
J. Biol. Chem., 250, 1824 (1975).
Carbohydrate Sulfate, (1918) 148, Am. Chem. Soc.
J. Biol. Chem. 243, 1523 (1968).

*Primary Examiner*—David M. Naff
*Assistant Examiner*—Mike Meller
*Attorney, Agent, or Firm*—Sughrue, Mion, Zinn, Macpeak & Seas

[57] ABSTRACT

Glycosaminoglycan degrading enzymes are fractionated and purified by chromatographically treating a solution containing the enzymes with an insoluble sulfated polysaccharide carrier. The enzymes are adsorbed onto the carrier and then subsequently desrobed from the carrier.

14 Claims, 1 Drawing Sheet

PURIFICATION OF GLYCOSAMINOGLYCAN DEGRADING ENZYMES WITH A SULFATED POLYSACCHARIDE

FIELD OF THE INVENTION

This invention relates to a method of purifying glycosaminoglycan degrading enzymes.

BACKGROUND OF THE INVENTION

It is so far known that cells of a glycosaminoglycan (GAG) degrading enzyme producer microorganism or culture media obtained upon cultivation of such microbial producer contain GAG degrading enzymes such as lyase, glycuronidase, sulfatase and other enzyme species.

An analytical method is also known for GAG sugar chain structure determination using lyase, glycuronidase, sulfatase and other enzyme species isolated from cells of the glycosaminoglycan degrading enzyme producer or culture media obtained upon cultivation of such producer (cf. Federation Proceedings, 36, 43 (1977); and The Journal of Biological Chemistry, 243, 1536 (1968)).

For the separation and purication of these enzymes from cell- and/or culture media-derived liquid preparations containing the same, there have been proposed a column chromatographic method using hydroxyapatite, a method using ion exchange chromatography and gel filtration combinedly, and a chromatographic method which utilizes the affinities of lyases, glycuronidases, sulfatases, etc. for immobilized heparin or dermatan sulfate (Carbohydrate Research, 70, 295, 1979; ibid., 88, 291, 1981), among others.

However, the column chromatographic method of separation and purification using hydroxyapatite is still disadvantageous in that it is difficult to separate the above-mentioned enzymes from one another, although the method is excellent in that impurities other than those enzymes can be removed efficiently therefrom.

The method using ion exchange chromatography and gel filtration combinedly can hardly separate *Flavobacterium haparinum*-derived heparitinase and sulfatase from each other or heparitinase and glycuronidase from each other. The chromatographic method using immobilized heparin or dermatan sulfate is also disadvantageous in that the column cannot be used repeatedly and in that the mutual separation of enzymes is unsatisfactory.

If enzymes separated and purified by such prior art methods are used for GAG sugar chain structure determination, serious errors may be made in GAG cleavage site determination or in sulfate group cleavage site determination since such enzymes are not sufficiently pure and each is not a single enzyme.

SUMMARY OF THE INVENTION

An object of the present invention is to provide a method of fractionating and purifying glycosaminoglycan degrading enzymes from a solution containing the same.

As a result of intensive investigation, the present inventors have found that GAG degrading enzymes can be isolated and purified by causing a glycosaminoglycan degrading enzyme to be adsorbed on an insoluble sulfated polysaccharide carrier and then desorbed from said carrier.

The present invention provides a method of purifying glycosaminoglycan degrading enzymes which comprises chromatographically treating glycosaminoglycan degrading enzymes on an insoluble sulfated polysaccharide carrier.

BRIEF DESCRIPTION OF THE DRAWINGS

In FIG. 1, each graphical curve has the following meanings.
—: $OD_{280}$
—: heparitinase activity
—: glycuronidase activity
In FIG. 2, each graphical curve has the following meanings.
—: $OD_{280}$
—: chondro-4-sulfatase activity
—: chondroitinase ABC activity

DETAILED DESCRIPTION OF THE INVENTION

Figure 1:
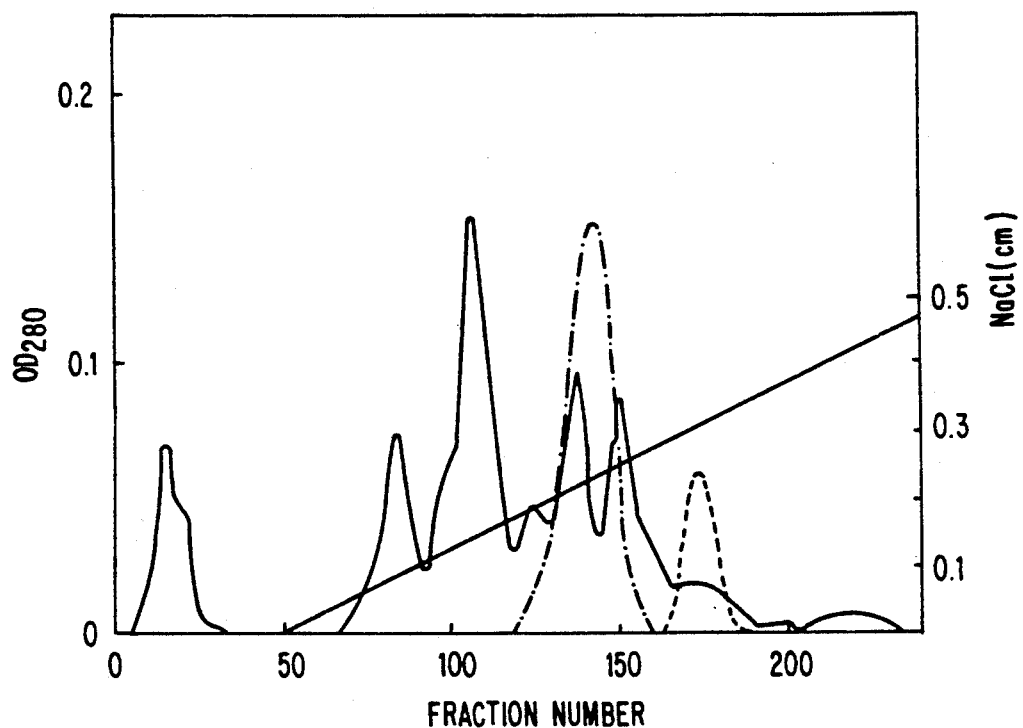
FIG. 1 shows the elution pattern for the chromatographic procedure of Example 2.

Glycosaminoglycan (GAG) degrading enzyme includes lyases, glycuronidases and sulfatases, among others.

As the lyases, there may be mentioned enzymes which act on an cleave the hexosaminide bond in glycuronan sulfates such as chodroitin sulfate lyases produced by microorganisms (e.g., chondroitinase ABC), dermatan sulfate lyases, heparan sulfate lyases (e.g., heparitinase), heparin lyases (e.g., heparinase).

As the glycuronidases, there may be mentioned enzymes which cleave off the uronic acid of the nonreducing terminal unsaturated sugar chain at the hexosaminide cleavage site as resulting from the action of a lyase on GAG.

As the sulfatases, there may be mentioned enzymes which cleave off a sulfate group of the decomposition products resulting from the action of one of the above-mentioned lyases and one of the above-mentioned glycuronidases, for example, chondro-4-sulfatase, chondro-6-sulfatase, glucosamine-N-sulfatase, glycuronate-2-sulfatase and glucosamine-3-sulfatase.

Examples of the GAG degrading enzymes-producing microorganisms used in the present invention include *Proteus valgaris*, *Flavobacterium heparinum* and *Arthrobacter aurescens*. These microorganisms can produce the following enzymes.

| Microorganism | Enzyme | Inducer |
| --- | --- | --- |
| *Proteus vulgaris* | Chondroitinase ABC | Chondroitin sulfate |
| | Chondro-4-sulfatase | |
| | Chondro-6-sulfatase | |
| *Flavobacterium heparinum* | Chondroitinase AC | Chondroitin sulfate |
| | Chondroitinase B | |
| | Chondroitinase C | |
| | Chondro-glycuronidase | |
| | Heparitinase I | Heparin |
| | Heparitinase II | |
| | Heparinase | |
| | Heparan-glycuronidase | |
| | Glycuronate-2-sulfatase | |
| | Glucosamine-3-sulfatase | |
| *Arthrobacter aurescens* | Chondroitinase AC II | |

*P. vulgaris*, *F. heparinum* and *A. aurescens* are cultivated in accordance with the method described in Methods in Enzymology 28, 902 (1972), Methods in Enzymology 28, 663 (1972) and The Journal of Biological Chemistry 250, 1824 (1975), respectively.

A preferred embodiment of the method of purification of GAG degrading enzymes according to the present invention can be carried out as follows.

A solution or culture medium containing a lyase, glycuronidase and/or sulfatase is applied to a hydroxyapatite or DEAE-cellulose column, then elution is carried out with phosphate buffer on a linear sodium chloride concentration gradient, and the resulting eluate containing the lyase, glycuronidase and/or sulfatase as a major solute component is applied to an insoluble sulfated polysaccharide carrier column. A sulfatase-containing solution can be obtained as the effluent of passthrough fraction. The lyase and glycuronidase which are adsorbed on the carrier can be separately fractionated by eluting with an aqueous solution by linearly increasing concentration of sodium chloride. The linear sodium chloride concentration according to the present invention ranges from 0 to 0.5 M.

The purification method according to the present invention is suitably applied to the separation and purification of chondrortinase ABC and chondrosulfatase, hepatirinase I and chondroglycronidase, and heparinase and glycuronate-2-sulfatase.

The insoluble sulfated polysaccharide carrier may be a product prepared by sulfating one or more hydroxyl groups on the sugar chain of an aqueous solvent insoluble macromolecular polysaccharide, such as cellulose, dextran, xylan, mannan, amylose, chitin or the like, or by crosslinking a water-soluble polysaccharide and then sulfating one or more hydroxyl groups on the sugar chain of the polysaccharide insolubilized by crosslinking.

The usable as the insoluble sulfated polysaccharide carrier in the practice of the invention are, for example, sulfation products derived from commercially available polysaccharide base materials for chromatography such as Cellulofine (trademark; manufactured by Chisso Corp. and distributed by Seikagaku Kogyo), Sephadex (trademark; manufactured and distributed by Pharmacia) and Sepharose (trademark; manufactured and distributed by Pharmacia), and products derived from soluble polysaccharides by sulfation following crosslinking for insolubilization with epichlorohydrin or the like. The kind of polysaccharide, the method of insolubilization or the method of sulfation is not critical in the practice of the invention.

The sulfation may be carried out in the conventional manner which comprising, for instance, suspending polysaccharides in a solvent, such as pyridine, chloroform, formamide, dimethylformamide or dimethyl sulfoxide and sulfaging the polysaccharides with a sulfating agent such as chlorosulfonic acid or sulfur trioxide or a complex of such sulfating agent with an organic salt thereof (cf. "Carbohydrate Sulfate" (1918) 148, American Chemical Society, Washington D.C.).

Various sulfated polysaccharides differing in degree of sulfation can be obtained by varying the quantity of the sulfating agent or a complex of the sulfating agent and an organic salt thereof e.g., sulfur trioxide-pyridine complex, the reaction temperature, the reaction time and other factors.

In the practice of the invention, the insoluble sulfated polysaccharide preferably has a sulfate group content within the range of from 0.1 to 1% by weight on the dried basis.

For example, when sulfur trioxide-pyridine complex is used in an amount of 1 to 10% by weight based on the weight of dry powder of the polysaccharide, the insoluble sulfated polysaccharide having a sulfate group content of 0.1 to 1% by weight can be obtained. The reaction temperature for sulfation is varied depending on the solvent used. When pyridine, dimethylformamide or formamide is used as a solvent, the reaction may be carried out for 1 to 3 hours at a temperature of 70° C. or more, 40°-60° C. and 30° C. or less, respectively.

The chromatographic method using such insoluble sulfated polysaccharide carriers for the enzyme purification of the present invention can be carried out by general procedures so far used in ion exchange chromatography, either batchwise or in the manner of column chromatography. The enzymes are adsorbed on these carriers and then desorbed. The eluent to be used in this procedure include buffers having the pH range of 5.0 to 9.5, such as acetate buffer, phosphate buffer and Tris-hydrochloride buffer. The enzyme separation pattern may be varied depending on the buffer used.

The purification method according to the invention can fractionate and purify a variety of useful enzymes efficiently. While the prior art ligands which are glycosaminoglycans (GAG) themselves immobilized by means of GAG-immobilizing carriers are susceptible to enzymatic degradation, the insoluble sulfated polysaccharide carriers which are to be used in accordance with the present invention are advantageous in that they are stable, that they can be regenerated readily by merely washing columns thereof with a salt solution and that they are so inexpensive that they can be used in large quantities.

The following examples further illustrate the present invention in detail, but are not to be construed to limit the scope thereof.

PRODUCTION EXAMPLE 1

Sephadex G-50 (5 g; Pharmacia) was suspended in 100 ml of formamide. To the solution was added a cooled formamide solution (100 ml) containing 2.5 ml of chlorosulfonic acid. The mixture was stirred at 30° C. for 5 hours, about 200 ml of ice water was then added, and the pH was adjusted to 7.0 by dropwise addition of 2 M sodium carbonate. The solid phase was collected by filtration using a glass filter and washed thoroughly with cold water to give sulfated Sephadex. The thus-obtained sulfated product was dehydrated using ethanol and dried. The sulfate group content of the dried product was found to be 0.8% by weight.

PRODUCTION EXAMPLE 2

Swollen Cellulofine GCL-90 (trademark; manufactured by Chisso Corp. and distributed by Seikagaku Kogyo) was suctioned on a glass filter for dehydration. Methanol was then added thereto for effecting a sufficient extent of dehydration. After washing with ether for removing the remaining methanol, the dehydration product was dried under vacuum. A 5-gram portion of the thus-obtained dry Cellulofine powder was suspended in 100 g of dimethylformamide. To the suspension was added 0.125 g of sulfur trioxide-pyridine complex. The sulfation reaction was carried out at 45°-55° C. for about 1 hour and then the reaction mixture was filtered using a glass filter. The solid on the filter was washed thoroughly with a methanol solution. The powder thus obtained was suspended in water, the suspension was adjusted to pH 8 by dropwise addition of 0.1 N sodium hydroxide solution for conversion of the sulfation product to the sodium salt form. Thorough washing with water gave 4.6 g (dried weight) of sulfated Cellulofine, the sulfate group content of which was 0.2% weight.

EXAMPLE 1

*Flavobacterium heparium* (ATCC. 13125, NCIB-9290) was cultivated at 30° C. for 18 hours in 100 l of a medium (pH 7.0) containing 1.5% peptone, 0.45% meat extract, 1.0% yeast extract and 1.0% malt extract. Then, heparin (Nakarai Chemical) was added to this culture medium so as to give the final concentration of 0.02% and the resulting medium was further incubated for 6 hours. After cultivation, the culture medium was centrifuged to obtain 1.5 kg (wet basis) of the bacterial cells. Then, 1 kg of the resulting cells (wet basis) were suspended in 3 kg of 0.7 M sodium acetate solution. The cells were desrupted with Dynomill (Willy A. Bachhofen Co.) and the thus-obtained suspension was centrifuged at 10,000 rpm for 30 minutes. The supernatant was collected and dialyzed against distilled water. The dialysate was centrifuged at 10,000 rpm for 30 minutes and the resulting supernatant was lyophilized to obtain 50 g of the lyophilization powder of a crude enzyme extract. This was used as the starting material. A 5-gram portion of this powder was dissolved in 1 liter of 50 mM phosphate buffer (pH 6.8) and the solution was applied to a hydroxyapatite column (6 × 20 cm) equilibrated with the same buffer. The column was washed with 2 liters of the same buffer and then elution was carried out by the linear concentration gradient method using 3 liters of the same buffer while adding thereto a total of 3 liters of 0.5 M sodium chloride. Eluate fractions were assayed for activity using heparin as the substrate. Fractions showing heparinase activity (eluent sodium chloride concentration range about 0.12 M to 0.2 M) were pooled and then desalted and concentrated using an ultrafiltration membrane. The ultrafiltration membrane was washed with 50 mM Tris-hydrochloride buffer (pH 7.5). The concentrate and washings were combined and water was added thereto to make a total volume of 100 ml. To this solution was added 20 g (wet weight) of sulfated Sephadex G-50 prepared in Production Example 1 equilibrated in advance with the same buffer. The mixture was stirred gently at 5° C. for 1 hour, then transferred to a 2 × 10 cm column, and washed with the same buffer, whereby glycuronate-2-sulfatase appeared in the effluent. The column was then washed with 0.2 M sodium chloride and heparinase was eluted with 0.5 M sodium chloride. The active fractions obtained are shown in Table 1.

Each enzyme activity was measured in the following manner (the same assay method was used in the following examples).

(a) Heparinase activity assay: A mixture of 25 μl of an aqueous solution of porcine intestinal mucosa-derived heparin (Heparin Sodium Salt (Porcive Intestinal Mucosa) manufactured by Sigma) (10 mg/ml), 25 μl of the enzyme solution and 50 μl of 20 mM acetate buffer (pH 7.0) containing 2 mM calcium acetate is incubated at 37° C. for 10 minutes. Immediately thereafter, 500 μl of 0.06 N hydrochloric acid is added and the absorption maximum at 232 nm is measured. One unit of potency is defined as the quantity of enzyme which causes formation of 1 micromole of unsaturated uronic acid per minute.

(b) Heparitinase (heparan sulfate lyase) activity assay: The procedure is the same as in the case of heparinase activity assay except that heparan sulfate is used as the substrate.

(c) Glycuronate-2-sulfatase activity assay: A solution of 1 ml of imidazole buffer (pH 6.5) containing 2.8 mg of ΔDi-diS$_D$ (Seikagaku Kogyo) is used as the substrate. To 10 μl of this solution is added 20 μl of the enzyme solution. After 15 minutes of incubation at 37° C, the reaction mixture is heated at 100° C. for 1 minute for terminating the reaction. A 20-μl portion of the reaction mixture is subjected to high-performance liquid chromatography and the quantity of ΔDi-6S resulting from degradation is determined based on the absorbance at 232 nm. One unit of potency is defined as the enzyme activity causing formation of 1 micromole of ΔDi-6S per minute.

(d) Glycuronidase activity assay: A mixture of 10 μl of ΔDi-6S (Seikagaku Kogyo) (2 mg/ml), 10 μl of 0.2 M Tris-hydrochloride buffer (pH 7.5) and 10 μl of the enzyme solution is incubated at 37° C. for 15 minutes and then heated at 100° C. for 1 minute for terminating the reaction. A 20-μl portion of the reaction mixture is subjected to high-performance liquid chromatography and the activity is calculated based on the decrement in absorbance at 232 nm. One unit of enzymatic potency is defined as the activity causing degradation of 1 micromole equivalent of unsaturated sugar per minute.

(e) Chondroitinase ABC and chondro-4-sulfatase assay: The method described in J. Biol. Chem., 243, 1523 (1968) is used.

TABLE 1

| Fraction | Total OD$_{280}$ | Heparinase activity | Glycuronate 2-sulfatase activity |
| --- | --- | --- | --- |
| Before fractionation | 95 | 148 units | 3.8 units |
| Unadsorbed fraction | 73 | 0 | 3.2 |
| 0.2 M sodium chloride eluate fraction | 7.5 | 0 | 0 |
| 0.5 M sodium chloride eluate fraction | 3.2 | 116 | 0 |

EXAMPLE 2

The eluate fractions from the hydroxyapatite column as obtained in Example 1 were checked for activity using heparan sulfate as the substrate. Heparitinase fractions (sodium chloride concentration range about 0.25 to 0.32 M) were pooled and then concentrated and desalted using an ultrafiltration membrane. The membrane was washed with 50 mM Tris-hydrochloride buffer (pH 7.2). The concentrate and washings were combined and applied to a sulfated Cellulofine (prepared in Production Example 2) column (2.2 × 30 cm) equilibrated with the same buffer. The column was washed with the same buffer and then elution was carried out using the same buffer supplemented with sodium chloride to make a linear sodium chloride concentration gradient up to a final sodium chloride concentration of 0.4 M.

Since the pooled heparitinase fraction before application thereof to the column contained a glycuronidase species, the glycuronidase activity was measured using ΔDi-6S as the substrate. The elution pattern thus obtained for the above chromatographic procedure is shown in FIG. 1.

As a result of this chromatography, the specific activity of heparitinase and that of glycuronidase increased by 6 times and 18 times, respectively, as compared before chromatography.

EXAMPLE 3

*Proteus vulgaris* (NCTC 4636) was cultivated at 30° C. for 12 hours under aeration in 20 l of a medium containing 300 g of peptone, 90 g of meat extract, 30 g of sodium chloride and 100 g of a crude chondroitin sulfate derived from shark cartilage. The cultured medium was centrifuged at 5° C. to obtain 150 g (wet basis) of cells. The cells were suspended in 500 ml of 20 mM Tris-hydrochloride buffer (pH 7.2), subjected to disruption with Dynomill (Willy A. Bachhofen Co.) and centrifuged to obtain 460 ml of a crude enzyme extract. An equivolume of a protamine-containing solution (125 mg/l) was added thereto. After standing the mixture for 30 minutes, centrifugeation was carried out to remove the insoluble matter. Then, ammonium sulfate was added to the resulting supernatant and the precipitate formed between 35 and 65% saturation with ammonium sulfate was collected by centrifugation. The precipitate was dissolved in 100 ml of 50 mM Tris-hydrochloride buffer (pH 7.2) and this solution was subjected to dialysis against the same buffer. The dialysate was applied to a DEAE-cellulose column (6 × 40 cm) equilibrated with the same buffer. After washing the column with the same buffer, the fractions showing chondroitinase ABC. and chondro-4-sulfatase activity were collected and concentrated to 40 ml using an ultrafiltration membrane. The thus-obtained concentrate was centrifuged to remove the insoluble matter.

Figure 2:
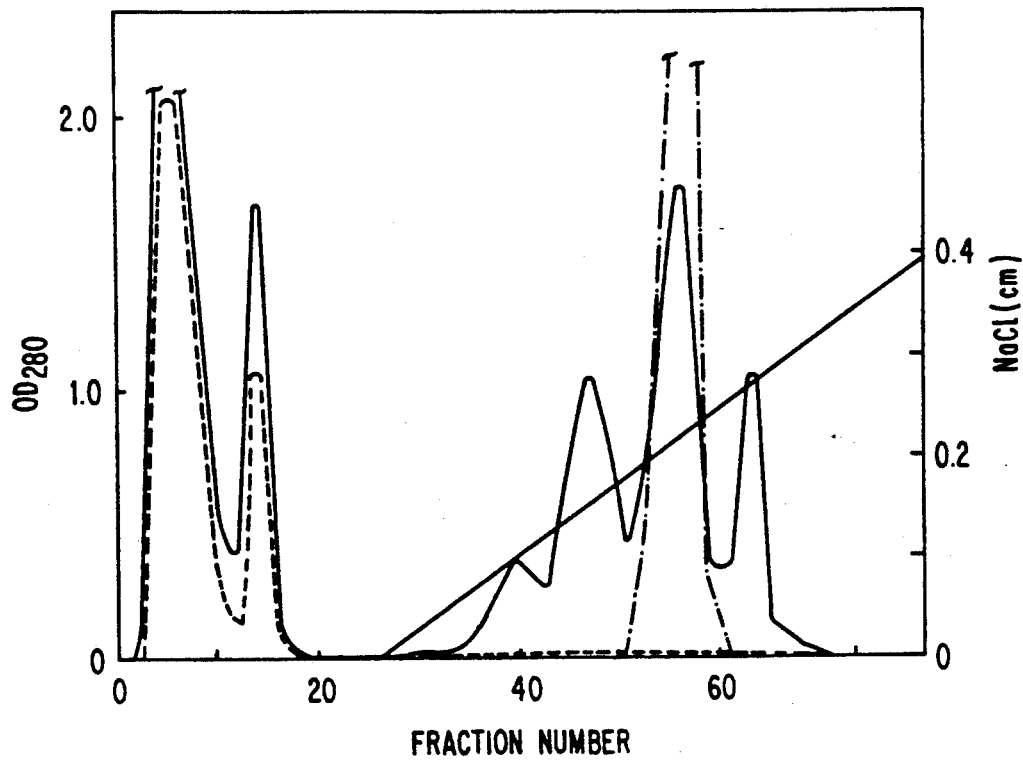
FIG. 2 shows the eulution pattern for the chromatographic procedure of Example 3.

This concentrate was applied to a sulfated Cellulofine (prepared in Production Example 2) column (2.2 × 22 cm) equilibrated with 50 mM Tris-hydrochloride buffer (pH 7.2). The column was washed with the same buffer and elution was then carried out with the same buffer with sodium chloride added to increase the sodium chloride concentration from 0 to 0.4 M, whereby chondro-4-sulfatase was removed and the specific activity of chondroitinase ABC. was increased by about 12 times. The elution pattern for this chromatography is shown in FIG. 2.

The chondroitinase ABC. activity yield and the specific activity of the product are shown in Table 2.

TABLE 2

| | Total activity | Total $OD_{280}$ | Specific activity |
|---|---|---|---|
| Before chromatography | 6,700 units | 422 | 15.9 |
| After chromatography | 5,980 units | 30.6 | 195 |

While the invention has been described in detail and with reference to specific examples thereof, it will be apparent to one skilled in the art that various changes and modifications can be made therein without departing from the spirit and scope thereof.

What is claimed is:

1. A method of purifying glycosaminoglycan degrading enzymes by fractionating the glycosaminoglycan degrading enzymes into individual glycosaminoglycan degrading enzymes which comprises chromatographically treating a solution containing the glycosaminoglycan degrading enzymes with an insoluble sulfated polysaccharide carrier whereby said glycosaminoglycan degrading enzymes are adsorbed onto said insoluble sulfated polysaccharide carrier, produced by sulfination of a polysaccharide whereafter said adsorbed glycosaminoglycan degrading enzymes are desorbed from said insoluble sulfated polysaccharide carrier.

2. A method as claimed in claim 1, wherein the glycosaminoglycan degrading enzymes include at least two enzymes selected from the group consisting of a lyase, glycuronidase and sulfatase.

3. A method as claimed in claim 1, wherein the insoluble sulfated polysaccharide carrier is prepared by sulfating one or more hydroxyl groups on the sugar chain of the polysaccharide selected from the group consisting of cellulose, dextran, xylan, mannan, amylose and chitin.

4. A method as claimed in claim 1, wherein the insoluble sulfated polysaccharide carrier is prepared by crosslinking a water-soluble polysaccharide and then sulfating one or more hydroxyl groups on the sugar chain.

5. A method as claimed in claim 1, wherein the insoluble sulfated polysaccharide carrier has a sulfate group content ranging from 0.1 to 1% by weight on dried basis.

6. A method of purifying a lyase, glycuronidase and/or sulfatase which comprises loading a hydroxyapatite or DEAE-cellulose column with a lyase-, glycuronidase-and/or sulfatase-containing solution, performing elution with a phosphate buffer on a linear sodium chloride concentration gradient, then applying the resulting eluate containing the lyase, glycuronidase and/or sulfatase as a major solute component to a column containing an insoluble sulfated polysaccharide carrier produced by sulfination of a polysaccharide and recovering a sulfatase solution as the effluent or pass-through fraction and/or eluting the lyase and the glycuronidase with an aqueous sodium chloride solution by linear sodium chloride concentration gradient and recovering the lyase and the glycroronidase as separate fractions.

7. A method as claimed in claim 5, wherein the insoluble sulfated polysaccharide carrier is prepared by sulfating one or more hydroxyl groups on the sugar chain of cellulose, dextran, xylan, mannan, amylose or chitin or by crosslinking a water-soluble polysaccharide for insolubilization and then sulfating one or more hydroxyl groups on the sugar chain.

8. A method as claimed in claim 6, wherein the lyase is a chondroitin sulfate lyase, dermatan sulfate lyase, heparan sulfate lyase or heparin lyase.

9. A method as claimed in claim 8, wherein the chondroitin sulfate lyase is chondroitinase ABC.

10. A method as claimed in claim 8, wherein the heparan sulfate lyase is heparitinase.

11. A method as claimed in claim 8, wherein the heparin lyase is heparinase.

12. A method as claimed in claim 6, wherein the glycuronidase is an enzyme capable of cleaving off the uronic acid of the nonreducing terminal unsaturated sugar chain at the hexosaminide cleavage site resulting from the action of a lyase on a glycosaminoglycan.

13. A method as claimed in claim 6, wherein the sulfatase is chondro-4-sulfatase, chondro-6-sulfatase, glucosamine-N-sulfatase, glycuronate-2-sulfatase or glucosamine-3-sulfatase.

14. A method as claimed in claim 6, wherein the insoluble sulfated polysaccharide carrier has a sulfate group content ranging from 0.1 to 1% by weight on dried basis.

* * * * *